(12) United States Patent
Vanderpool et al.

(10) Patent No.: US 11,311,312 B2
(45) Date of Patent: *Apr. 26, 2022

(54) SUBCUTANEOUS DELIVERY TOOL

(71) Applicant: Medtronic, Inc., Minneapolis, MN (US)

(72) Inventors: Matthew T. Vanderpool, Minneapolis, MN (US); Michael R. Klardie, Plymouth, MN (US); Kris A. Peterson, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 72 days.

This patent is subject to a terminal disclaimer.

(21) Appl. No.: 14/204,227

(22) Filed: Mar. 11, 2014

(65) Prior Publication Data

US 2014/0276928 A1 Sep. 18, 2014

Related U.S. Application Data

(60) Provisional application No. 61/788,940, filed on Mar. 15, 2013.

(51) Int. Cl.
*A61B 17/3209* (2006.01)
*A61B 17/32* (2006.01)
(Continued)

(52) U.S. Cl.
CPC .... *A61B 17/3468* (2013.01); *A61B 17/32093* (2013.01); *A61B 5/283* (2021.01);
(Continued)

(58) Field of Classification Search
CPC ............... A61B 5/042; A61B 17/3468; A61B 2017/3492; A61B 2560/063; A61M 37/0069; A61N 1/3756; A61N 1/37205
See application file for complete search history.

(56) References Cited

U.S. PATENT DOCUMENTS

| 2,009,393 | A | * | 7/1935 | Gioacchino | A61M 37/0069 604/60 |
| 4,915,686 | A | | 4/1990 | Frederick | |

(Continued)

FOREIGN PATENT DOCUMENTS

| CN | 1031481 A | 3/1989 |
| CN | 2621634 Y | 6/2004 |

(Continued)

OTHER PUBLICATIONS (PCT/US2014/023912) PCT Notification of Transmittal of the International Search Report and the Written Opinion of the International Searching Authority, dated Jun. 20, 2014, 9 pages.

(Continued)

*Primary Examiner* — Jing Rui Ou
(74) *Attorney, Agent, or Firm* — Shumaker & Sieffert, P.A.

(57) ABSTRACT

Subcutaneous implantation tools and methods of implanting a subcutaneous device using the same. The tool may include a tool body having a longitudinally extending recess having a distal opening and having a tunneler at a distal end of the tool body extending from the distal opening of the recess. The tool may include a plunger slidably fitting within at least a portion of the tool body recess. The recess may be configured to receive an implantable device and the tunneler preferably extends distally from the recess at a position laterally displaced from the device when the device is so located in the recess. Movement of the plunger distally within the recess advances the device distally out of the recess and alongside of and exterior to the tunneler.

23 Claims, 9 Drawing Sheets

(51) Int. Cl.
  *A61B 17/34* (2006.01)
  *A61N 1/375* (2006.01)
  *A61N 1/372* (2006.01)
  *A61B 5/283* (2021.01)

(52) U.S. Cl.
  CPC ............. *A61B 2017/320044* (2013.01); *A61B 2017/320056* (2013.01); *A61N 1/3756* (2013.01); *A61N 1/37205* (2013.01)

(56) References Cited

U.S. PATENT DOCUMENTS

| | | | |
|---|---|---|---|
| 5,127,404 A | 7/1992 | Wyborny et al. | |
| 5,304,119 A * | 4/1994 | Balaban | A61M 37/0069 604/107 |
| 5,484,403 A | 1/1996 | Yoakum et al. | |
| 5,562,613 A | 10/1996 | Kaldany | |
| 5,772,671 A * | 6/1998 | Harmon | A61M 37/0069 604/60 |
| 5,842,999 A | 12/1998 | Pruitt et al. | |
| 5,954,670 A | 9/1999 | Baker | |
| 5,987,352 A | 11/1999 | Klein et al. | |
| 6,230,059 B1 | 5/2001 | Duffin | |
| 6,412,490 B1 | 7/2002 | Lee | |
| 7,035,684 B2 | 4/2006 | Lee | |
| 8,888,745 B2 | 11/2014 | Van Der Graaf et al. | |
| 10,786,279 B2 | 9/2020 | Vanderpool et al. | |
| 2001/0029386 A1 | 10/2001 | Matsutani et al. | |
| 2004/0082969 A1 | 4/2004 | Kerr | |
| 2004/0193154 A1 | 9/2004 | Leatherbury et al. | |
| 2004/0249388 A1* | 12/2004 | Michelson | A61B 17/025 606/90 |
| 2005/0090852 A1* | 4/2005 | Layne | A61B 17/3417 606/190 |
| 2005/0096645 A1* | 5/2005 | Wellman | A61B 17/320016 606/41 |
| 2005/0107768 A1* | 5/2005 | Ting | A61M 31/007 604/506 |
| 2006/0074434 A1* | 4/2006 | Wenstrom, Jr. | A61B 17/17 606/96 |
| 2006/0097331 A1 | 5/2006 | Hattori et al. | |
| 2006/0106415 A1 | 5/2006 | Gabbay | |
| 2006/0174898 A1 | 8/2006 | Brown | |
| 2007/0010738 A1 | 1/2007 | Mark et al. | |
| 2007/0179515 A1* | 8/2007 | Matsutani | A61B 17/3211 606/167 |
| 2007/0249992 A1 | 10/2007 | Bardy | |
| 2008/0154298 A1* | 6/2008 | Grayzel | A61B 17/02 606/190 |
| 2009/0030426 A1* | 1/2009 | Zinn | A61B 17/3415 606/108 |
| 2009/0036917 A1* | 2/2009 | Anderson | A61B 5/0031 606/185 |
| 2009/0137946 A1* | 5/2009 | Nassiri | A61B 17/3472 604/60 |
| 2010/0030227 A1* | 2/2010 | Kast | A61B 17/3468 606/129 |
| 2010/0094252 A1 | 4/2010 | Wengreen et al. | |
| 2010/0198140 A1* | 8/2010 | Lawson | A61F 2/4601 604/57 |
| 2010/0324578 A1 | 12/2010 | Bardy | |
| 2010/0331868 A1 | 12/2010 | Bardy | |
| 2012/0283705 A1 | 11/2012 | Lee et al. | |
| 2014/0128963 A1 | 5/2014 | Quill et al. | |
| 2016/0175007 A1 | 6/2016 | Valbuena et al. | |
| 2017/0258346 A1 | 9/2017 | Vanderpool et al. | |
| 2020/0129206 A1 | 4/2020 | Cornelius et al. | |
| 2020/0383702 A1 | 12/2020 | Vanderpool et al. | |
| 2021/0153895 A1 | 5/2021 | Vanderpool et al. | |
| 2021/0267634 A1 | 9/2021 | Vanderpool et al. | |
| 2021/0267635 A1 | 9/2021 | Vanderpool et al. | |
| 2021/0267636 A1 | 9/2021 | Vanderpool et al. | |
| 2021/0275221 A1 | 9/2021 | Vanderpool et al. | |

FOREIGN PATENT DOCUMENTS

| | | |
|---|---|---|
| CN | 2702718 Y | 6/2005 |
| CN | 20234297 U | 7/2012 |
| DE | 469951 C | 1/1929 |
| DE | 4243641 A1 | 9/1994 |
| EP | 3034128 A1 | 6/2016 |
| JP | 2001502937 A | 3/2001 |
| JP | 2007516031 A | 6/2007 |
| JP | 2008528084 A | 7/2008 |
| JP | 201192065 A | 5/2011 |
| WO | 9813091 A1 | 4/1998 |
| WO | 2005044116 A2 | 5/2005 |
| WO | 2005060306 A1 | 6/2005 |
| WO | 2008016551 A1 | 2/2008 |
| WO | 2009018008 A2 | 2/2009 |
| WO | 2012/098356 A1 | 7/2012 |

OTHER PUBLICATIONS

First Office Action and Search Report, and translation thereof, from counterpart Chinese Application No. 201480015082.5, dated Mar. 20, 2017, 18 pp.

International Preliminary Report on Patentability from International Application No. PCT/US2014/023912, dated Sep. 15, 2015, 5 pp.

Office Action, and translation thereof, from counterpart Japanese Patent Application No. 2016-501382, dated Oct. 29, 2017, 7 pp.

Notice on the Second Office Action, and translation thereof, from counterpart ON Application No. 201480015082.5, dated Mar. 5, 2018, 9 pp.

Office Action dated Jan. 12, 2018, from U.S. Appl. No. 15/610,076, 25 pp.

Response to Office Action dated Jan. 12, 2018, from U.S. Appl. No. 15/610,076, filed Mar. 28, 2018, 17 pp.

Final Office Action from U.S. Appl. No. 15/610,076, dated Jun. 21, 2018, 25 pp.

Amendment in Response to Office Action dated Jun. 21, 2018, from U.S. Appl. No. 15/610,076, filed Aug. 21, 2018, 19 pp.

Notice of Allowance from U.S. Appl. No. 15/610,076, dated Mar. 23, 2020, 16 pp.

Office Action, and translation thereof, from counterpart Japanese Application No. 2018137778, dated Feb. 6, 2020, 3 pp.

Advisory Action from U.S. Appl. No. 15/610,076, dated Aug. 31, 2018, 3 pp.

Extended European Search Report from counterpart European Patent Application No. 18188908.0, dated Oct. 19, 2018, 7 pp.

Final Office from U.S. Appl. No. 15/610,076, dated Jun. 10, 2019, 25 pp.

Response to Office Action dated Jan. 10, 2019, from U.S. Appl. No. 15/610,076, filed Mar. 8, 2019, 15 pp.

Response to Office Action dated Jun. 21, 2018, from U.S. Appl. No. 15/610,076, filed Aug. 21, 2018, 19 pp.

Examination Report from counterpart European Application No. 14717919.6, dated Jul. 28, 2017, 5 pp.

Communication Pursuant to Rules 161(1) and 162 EPC, dated Nov. 4, 2015, from counterpart European Application No. 14717919.6, 2 pp.

Intent to Grant dated Apr. 16, 2018, from counterpart European Application No. 14717919.6, 30 pp.

Notice of Reasons for Refusal and translation thereof, from counterpart Japanese Application No. 2018-137778, dated Jun. 25, 2019, 15 pp.

Preliminary Amendments filed in counterpart European Patent Application No. 14717919.6, filed on Oct. 9, 2015, 9 pp.

Response to Communication Pursuant to Rules 161(1) and 162 EPC, dated Nov. 4, 2015, from counterpart European Application No. 14717919.6, filed May 13, 2016 5 pp.

Response to Restriction Requirement dated Aug. 8, 2017, from U.S. Appl. No. 15/610,076, filed Oct. 3, 2017, 1 pp.

Response to Examination Report dated Jul. 28, 2017, from counterpart European Application No. 14717919.6, filed Dec. 6, 2017, 13 pp.

(56) References Cited

OTHER PUBLICATIONS

Response to Communication Pursuant to Rule 69 EPC dated Jan. 7, 2019 and the Extended European Search Report (EESR) forward on Oct. 19, 2018, from counterpart European Application No. 18188908.0, filed Apr. 15, 2019, 13 pp.
Decision to Grant and translation thereof, from counterpart Japanese Application No. 2016-501382, dated Jun. 26, 2018, 5 pp.
Advisory Action from U.S. Appl. No. 15/610,076, dated Jul. 18, 2019, 3 pp.
Response to Office Action dated Jun. 10, 2019, from U.S. Appl. No. 15/610,076, filed Jul. 2, 2019, 18 pp.
Decision to Grant from counterpart European Application No. 14717919.6, dated Jun. 9, 2018, 1 pp.
Decision on Reexamination from counterpart Chinese Application No. 201480015082.5, dated Sep. 11, 2019, 11 pp.
Third Office Action, and translation thereof, from counterpart Chinese Application No. 201480015082 5, dated Apr. 7, 2020, 13 pp.
Notice of Allowance from U.S. Appl. No. 15/610,076, dated Apr. 29, 2020, 2 pp.
Office Action from U.S. Appl. No. 15/610,076, dated Jan. 10, 2019, 23 pp.
The Decision on Rejection, and translation thereof, from counterpart Chinese Application No. 201480015082.5, dated Dec. 5, 2018, 14 pp.
Fourth Office Action, and translation thereof, from counterpart Chinese Application No. 201480015082.5, dated Jun. 22, 2020, 13 pp.
Notice of Allowance from U.S. Appl. No. 15/610,076, dated Jul. 20, 2020, 13 pp.
U.S. Appl. No. 29/748,593, filed Aug. 31, 2020, naming inventors Vanderpool et al.
U.S. Appl. No. 29/748,588, filed Aug. 31, 2020, naming inventors Vanderpool et al.
The Notification of Rejection, and translation thereof, from counterpart Chinese Application No. 2014-80015082.5, dated Nov. 4, 2020, 11 pp.
Examination Report from counterpart European Application No. 18188908.0, dated May 26, 2021, 7 pp.
Prosecution History from U.S. Appl. No. 17/323,298, dated Sep. 9, 2021, 14 pp.
Prosecution History from U.S. Appl. No. 17/325,873, dated Sep. 3, 2021, 14 pp.
Prosecution History from U.S. Appl. No. 17/325,904, dated Aug. 11, 2021 through Aug. 18, 2021, 25 pp.
Prosecution History from U.S. Appl. No. 17/329,986, dated Sep. 30, 2021, 17 pp.
Response to Examination Report from counterpart European Application No. 18188908.0, dated May 26, 2021, filed Sep. 30, 2021, 24 pp.
U.S. Appl. No. 29/803,137, filed Aug. 10, 2021.
U.S. Appl. No. 29/803,142, filed Aug. 10, 2021.
Notice of Allowance from U.S. Appl. No. 17/329,986, dated Oct. 21, 2021, 12 pp.
Communication pursuant to Article 94(3) EPC from counterpart European Application No. 18188908.0 dated Feb. 3, 2022, 5 pp.

\* cited by examiner

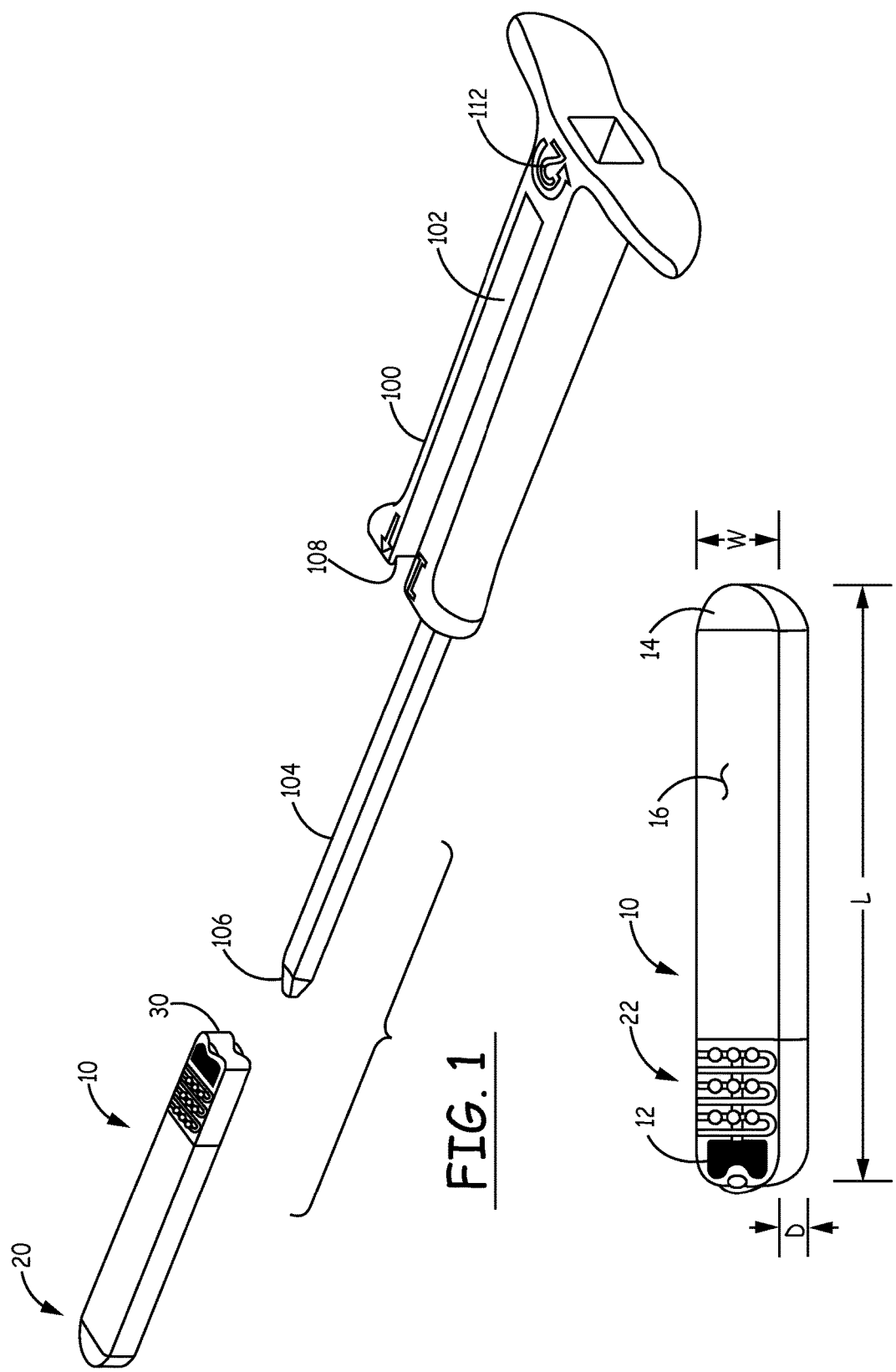

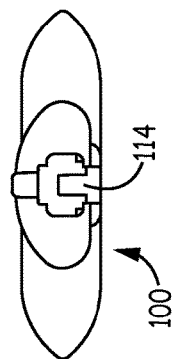 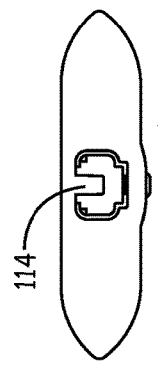
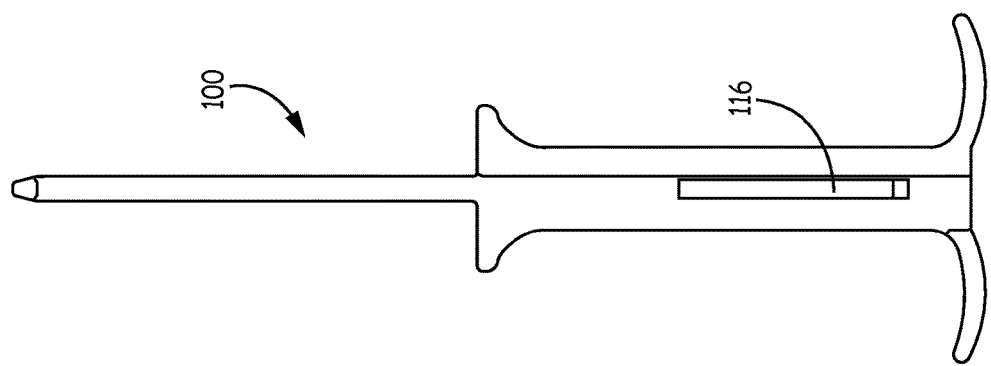
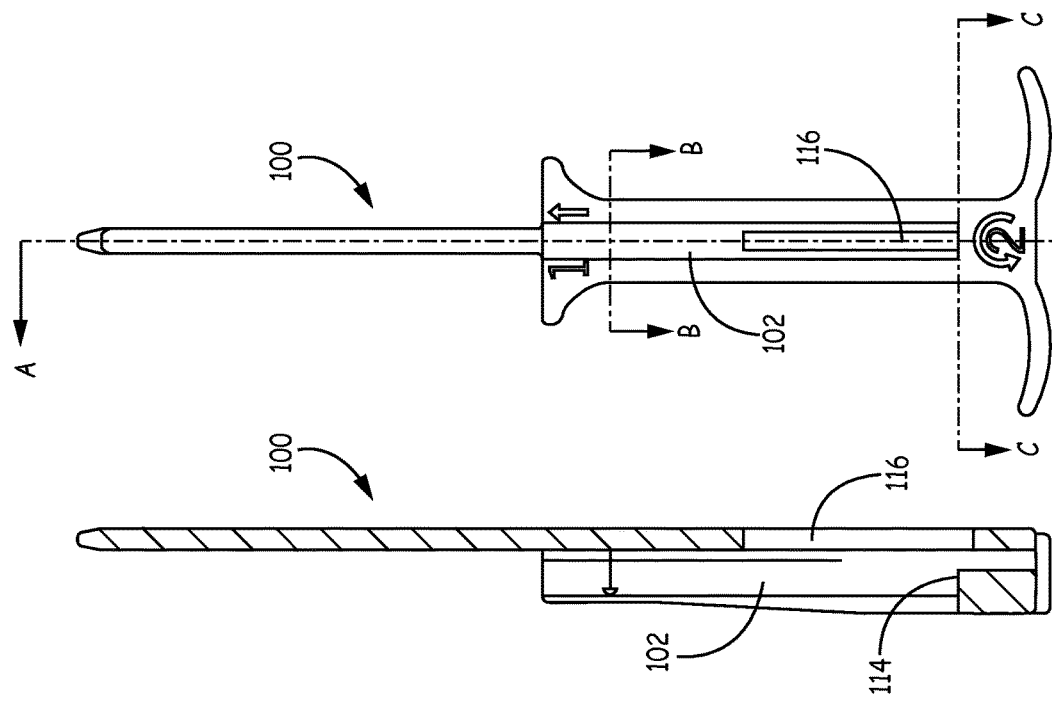

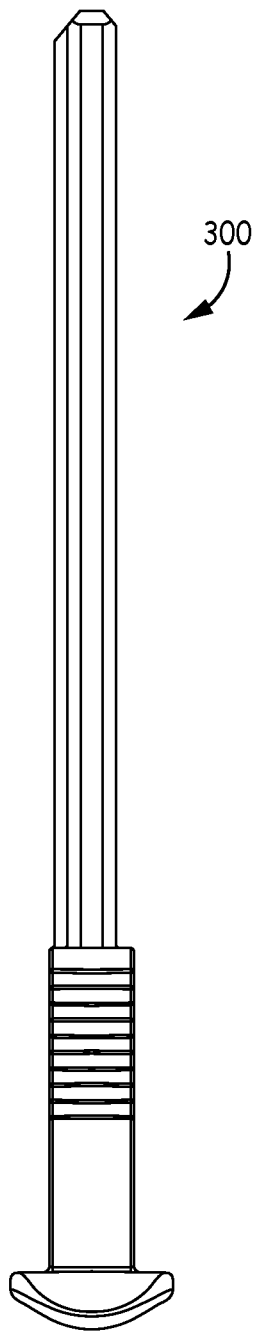
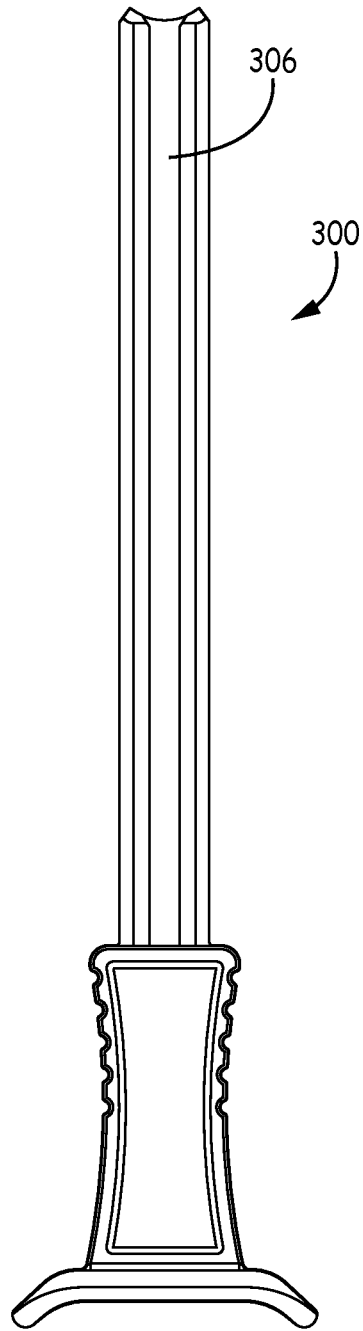
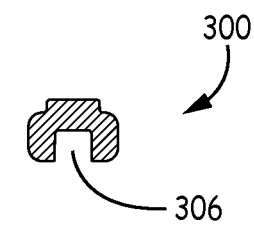
FIG. 9A
FIG. 9B
FIG. 9C

SUBCUTANEOUS DELIVERY TOOL

BACKGROUND

The use of monitoring equipment to measure various physical parameters of a patient is well known. There is a growing demand for using subcutaneous monitoring devices, which allow doctors to obtain information without a patient being connected to an external machine and/or which may otherwise not be reproducible in office settings. The term subcutaneous generally implies locations within the body of a patient under the skin and exterior to the musculature beneath the skin. For example, an implantable device that includes the ability to monitor a patient's heart beat in order to detect transient symptoms suggesting cardiac arrhythmia allows doctors to review data over a longer period of time than using external monitoring equipment in a simulated testing situation. However, to successfully implant implantable subcutaneous devices an implantation tool should, for example, ensure that the device is not implanted in muscle, reduce contact between the surgeon and the wound, be used in an office setting to minimize patient discomfort and the need for invasive surgery and have the ability to repeatedly recreate the same size incision site in the patient.

Exemplary prior art insertion tools include those illustrated in US Patent Application Publication No. 2010/0094252 by Wengreen, et al., incorporated herein by reference in its entirety.

SUMMARY

Further areas of applicability will become apparent from the description provided herein. It should be understood that the description and specific examples are intended for purposes of illustration only and are not intended to limit the scope of the present disclosure.

Exemplary embodiments provide subcutaneous implantation tools and methods of implanting a subcutaneous micro-device using the same. The invention provides a syringe-like tool, comprising a tool body, hereafter "handle", having a hollow, distally longitudinally extending recess such as a bore or channel and having a distal opening through which the device may be delivered. The device preferably also includes a movable plunger located within the bore or channel. An incision tool is provided to make an incision through which the subcutaneous device is implanted.

The device may, for example, be implanted in the region of the thorax. A specific recommended location will typically be provided within an associated product manual. In one embodiment, two electrodes on the body of the device monitor the patient's subcutaneous ECG. The device may ECG recordings in response to patient activation or in response to automatically detected arrhythmias. Exemplary devices are disclosed in US Patent Application Publication No. 2009/0036917 by Anderson, US Patent Application Publication No. 2010/0094252 by Wengreen, et al., US Patent Application Publication No. 2012/0283705 by Hoeppner, et al., U.S. Pat. No. 5,987,352, issued to Klein, et al., U.S. Pat. Nos. 6,412,490 and 7,035,684 issued to Lee, et al. and U.S. Pat. No. 6,230,059, issued to Duffin, et al., all incorporated herein by reference in their entireties.

The incision tool is designed to create an incision of repeatable width and depth with a single motion. It is composed of a blade, designed to make a repeatable incision, and handle, designed to ergonomically fit the hand. The incision tool is intended to make the incision simple and repeatable. Other mechanisms for making openings in the patient's skin such as trocars, spreaders, scalpels and the like may be substituted in some alternative embodiments.

The insertion tool delivers the device through the incision and into the subcutaneous tissue. The tool is designed to ensure the device is delivered into a tight pocket to maximize electrode contact with the surrounding tissue in a highly repeatable manner, and is composed of two parts: a handle and a plunger. The handle is composed of a bore or channel section, used to hold the device and guide it during implant, and a protrusion extending distally of the channel, used to bluntly dissect an implant path for the device to travel down while being implanted. The tunneler extends distally from the channel a position laterally displaced from the device when the device is located in the channel. The plunger is used to push the device distally out of the handle, through the incision, alongside and exterior to the tunneler and along the implant path created by the tunneler to the final implant location.

The device is typically loaded into the channel section of the insertion tool handle and sterile packaged along with both the insertion tool plunger and the incision tool The device is locatable within the channel distal to the plunger, so that when the plunger is moved distally, the device advances distally out of the tool body and into the tissue. Typically, the device will take the form of an elongated body, having a length greater than its thickness and width, as illustrated in the published Application No. 2010/0094252, cited above. The device may extend along its longitudinal axis between proximal and distal ends. The longitudinal channel or bore of the tool body may conform at least in part to the outer configuration of the device and more typically to a cross section of the device taken along its longitudinal axis. If the device, like the above discussed device, has a width greater than its depth and/or is otherwise radially asymmetric around its longitudinal axis, this feature allows the device to be advanced into the tissue while maintaining a desired orientation, as discussed in more detail below.

Optimally, the final insertion site of the device is located a short distance from the incision site. As noted above, the handle is preferably provided with an elongated protrusion or tunneler extending distally from the distal opening of the bore, which is insertable into the tissue through the incision to create a path in the tissue, along which the device may be advanced when pushed by the plunger. The distal end of the tunneler when so inserted is preferably located at the desired location of the distal end of the device. The length of the tunneler is thus preferably at least equal to and preferably somewhat greater than the length of the subcutaneous device.

Additional embodiments provide methods of implanting a subcutaneous micro-device, including inserting the dissection body of the tool described by the embodiments of the tool into an implantation site, where the dissection body includes a micro-device, and delivering the micro-device.

BRIEF DESCRIPTION OF THE DRAWINGS

Exemplary embodiments will be more clearly understood from the following detailed description taken in conjunction with the accompanying drawings. FIGS. 1-10 represent non-limiting, example embodiments as described herein.

FIG. 1 is a perspective view of an exemplary implantable device and the associated tool handle.

FIG. 2 is a perspective view of the exemplary implantable device;

FIG. 3 is a perspective view of the incision tool according to exemplary embodiments;

FIGS. 6A, 6B, 6C, 6D and 6E are distal end, cut-away, top, bottom and proximal end views, respectively, of the tool handle.

FIGS. 9A, 9B, and 9C are cross sectional, side and bottom views, respectively, of the plunger as illustrated in FIG. 8D.

FIG. 10 is a flow chart illustrating a method of delivering a device to a subcutaneous site according to exemplary embodiments.

DETAILED DESCRIPTION

Figure 3:
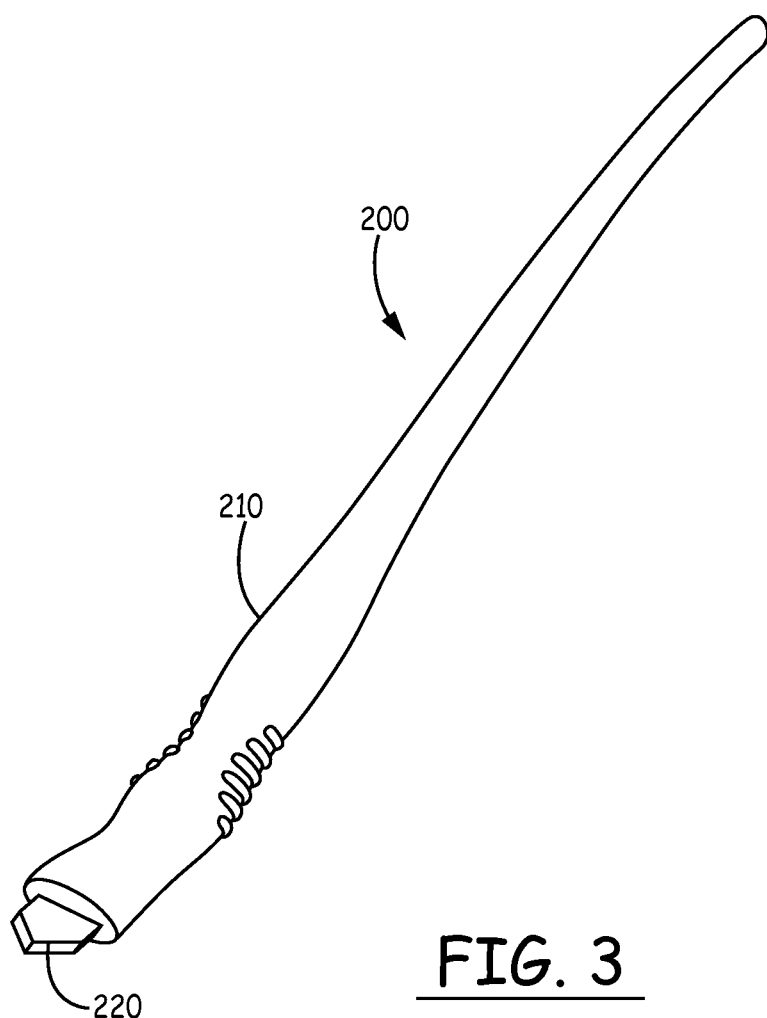

Various exemplary embodiments will now be described more fully with reference to the accompanying drawings in which some exemplary embodiments are illustrated. In the drawings, the thicknesses of layers and regions may be exaggerated for clarity.

Accordingly, while exemplary embodiments are capable of various modifications and alternative forms, embodiments thereof are shown by way of example in the drawings and will herein be described in detail. It should be understood, however, that there is no intent to limit exemplary embodiments to the particular forms disclosed, but on the contrary, exemplary embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of exemplary embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing only particular embodiments and is not intended to be limiting of exemplary embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, e.g., "beneath," "below," "lower," "above," "upper" and the like, may be used herein for ease of description to describe one element or a relationship between a feature and another element or feature as illustrated in the figures. It will be understood that the spatially relative terms are intended to encompass different orientations of the device in use or operation in addition to the orientation depicted in the Figures. For example, if the device in the figures is turned over, elements described as "below" or "beneath" other elements or features would then be oriented "above" the other elements or features. Thus, for example, the term "below" can encompass both an orientation which is above as well as below. The device may be otherwise oriented (rotated 90 degrees or viewed or referenced at other orientations) and the spatially relative descriptors used herein should be interpreted accordingly.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which exemplary embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Exemplary embodiments are directed to subcutaneous implantation tools and methods of implanting subcutaneous micro-devices. FIGS. 1A to 10 illustrate various exemplary embodiments of such subcutaneous implantation tools.

FIG. 1 shows the implantable device 10, aligned longitudinally with the handle 100, arranged for the insertion of device 10 into the channel 102 of the handle 100. The proximal end 20 of the device is inserted into the distal end 108 of the channel 102 of the handle and is advanced proximally until the proximal end 30 of the device is located adjacent an internal stop surface (not illustrated) within the handle 100. At this point, the distal end 20 of the device will be adjacent the proximal end of the 108 of the handle 100. The open upper portion of the channel 102 allows visual verification that the device 10 is properly inserted into the channel. The tunneler 104 extends distally of the distal end 108 of channel 102. The distal end 106 of the tunneler is placed into the incision made by the incision tool with its upper surface facing outward of the patient's body and advanced to provide blunt dissection of the subcutaneous tissue a point where the distal end 20 of the device is adjacent the opening of the incision. The handle 100 is then rotated 180 degrees so that the tunneler 104 is then above the device (outward relative to the patient's skin). This allows upward pressure on the handle to assist in temporarily enlarging the incision and assures that the device will not escape as advanced distally into the tissue. The device 10 is then advanced by distal movement of the plunger illustrated in FIG. 5B within the channel 102 and along the tunneler 104 until it is properly located within the tissue, displaced distally a short distance from the opening of the incision.

The logo 112 assists in reminding the physician to rotate the handle prior to insertion of the plunger and advancement of the device.

FIG. 2 shows the device 10 in more detail. In this view it can be seen that the device comprises two electrodes 12 and 14, located adjacent the proximal and distal ends, respectively, of the device. When implanted, electrode 12, located on the upper surface 16 of the device preferably faces outward toward the skin. As such, when the device is placed into the handle as discussed above, the electrode 12 faces downward and is not visible through the open upper portion of the channel, allowing verification of proper insertion into the handle.

The exemplary device 10 as illustrated generally takes the form of an elongated rectangular prism having rounded corners and a rounded distal end portion. The rounded distal end of the device assists in allowing it to advance into body tissue, providing blunt dissection of the tissue as it advances. Because the cross section of the device is substantially greater than the cross section of the tunneler, the device will be located snugly within the tissue, reducing the chances for the formation of air bubbles adjacent the electrodes and also assisting in maintaining the device in its desired position. The device has length (L), width (W) and depth (D) as illustrated. In this particular embodiment, the with is greater than the depth, providing radial asymmetry along the longitudinal axis of the device and assisting in maintaining the device in its proper orientation with upper surface 16 facing outward after implant. A suture hole 18 may optionally be provided at the proximal end of the device to allow the physician to suture it to underlying tissue if desired. Projections 22 may optionally be provided to prevent longitudinal movement of the device after implant.

As discussed above, the inner surface of the channel of the handle is preferably configured to correspond to the outer configuration of the device. As discussed below in more detail, the configuration of the channel of the handle is configured to engage the rounded corners of the device, preventing rotation of the device within the handle.

FIG. 3 illustrates the incision tool 200, which is provided with a curved plastic handle 210 fitted with a flat, pointed blade 220 having a width equal to the desired width of the incision. The handle is designed to be comfortably held in a position allowing the blade to be advanced through the skin at a shallow angle, avoiding damage to underlying muscle tissue.

Figure 4A:
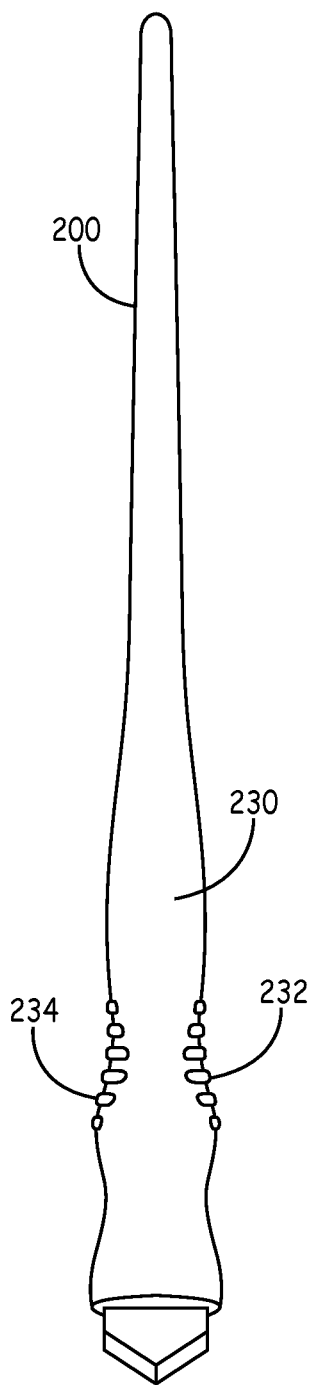
FIGS. 4A, 4B and 4C are top, side and bottom views, respectively, of the incision tool of FIG. 3.
Figure 4B:
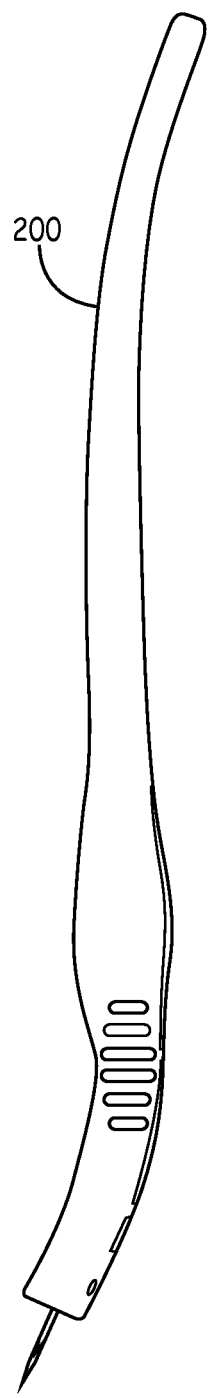
Figure 4C:
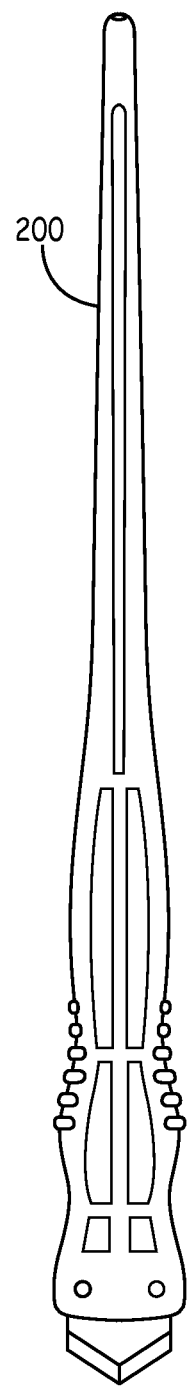

FIGS. 4A, 4B and 4C show top, side and bottom views of the incision device 200. As illustrated in 4A, both the differing coloration of the finger grips 234 and 232 and the placement of the logo 236 on the upper surface assist the physician in assuring that the orientation of the blade is correct to provide the desired shallow penetration angle.

Figure 5A:
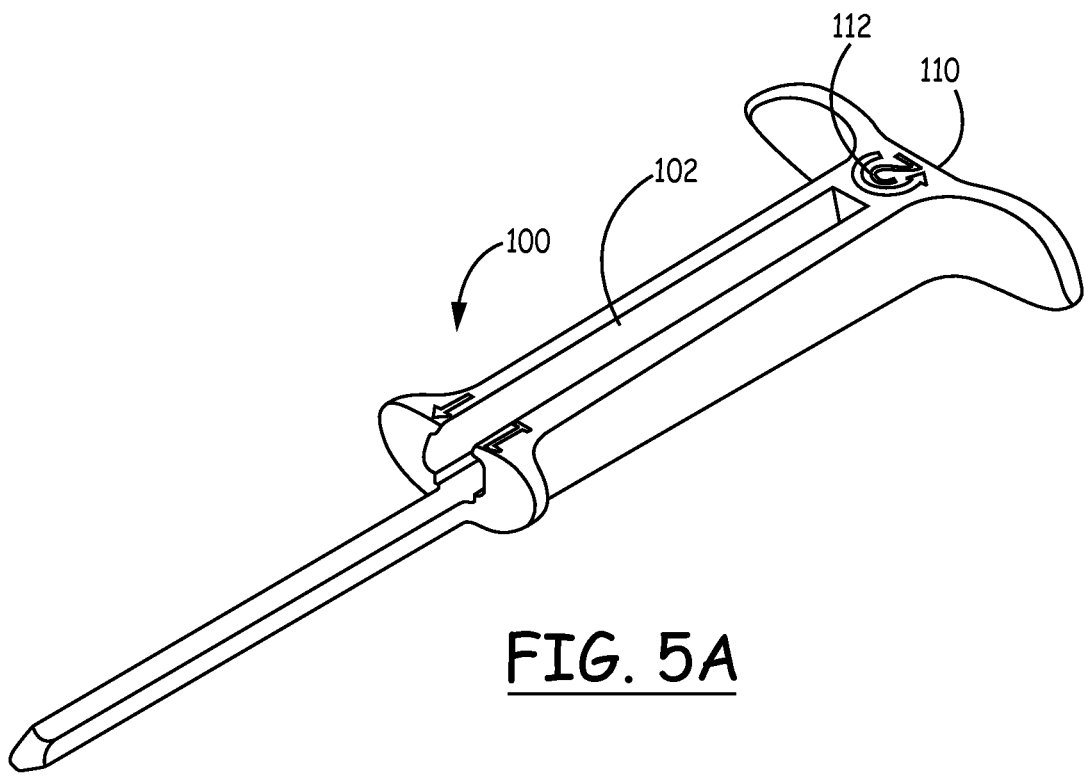
FIGS. 5A and 5B are perspective views of the tool handle and plunger, respectively, according to exemplary embodiments of the invention.
Figure 5B:
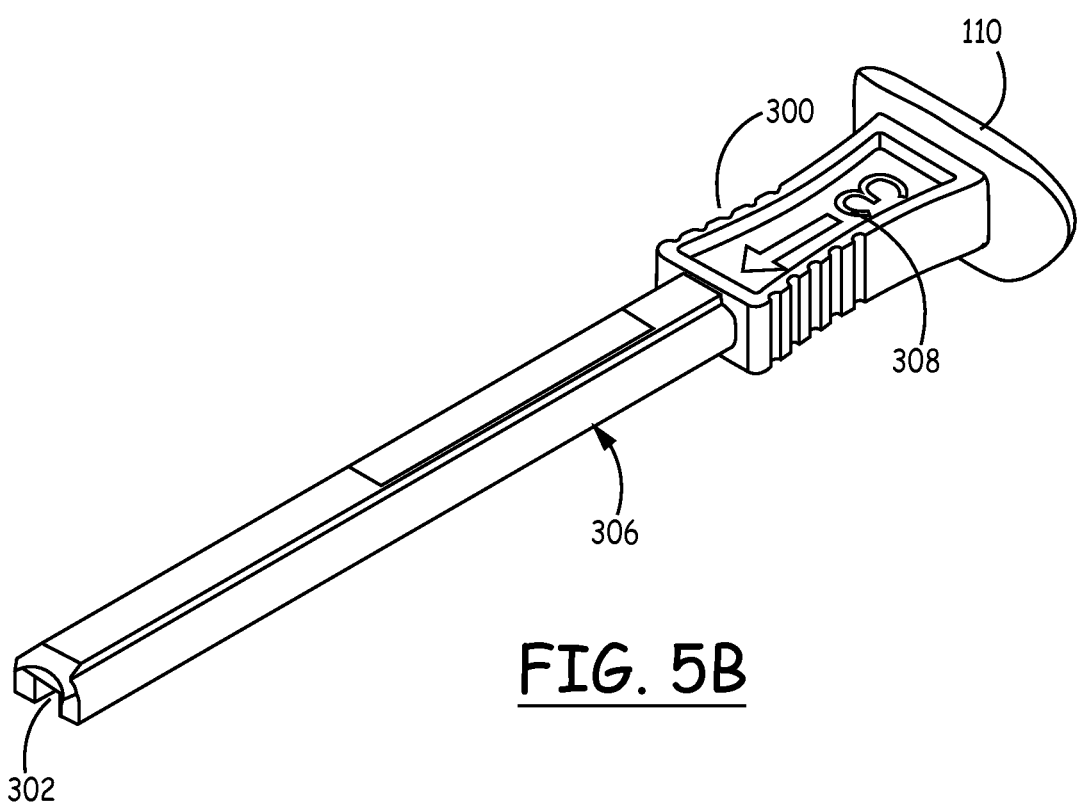

FIGS. 5A and 5B show the handle 100 and the plunger 300 prior to insertion of the plunger into the handle. After rotation of the handle so that its upper surface bearing marking 112 now faces inward toward the patient's skin, the distal end 302 of plunger 300 is then inserted into an opening in the proximal end 110 of the handle and into the channel 102 of the handle.

The plunger is provided with a groove 306 running the length of the lower surface of the plunger up to a distal stop surface discussed below. The opening in the proximal end of the handle includes a protrusion corresponding to the groove in the lower surface of the plunger, assuring its proper orientation within the handle. A marking 308 adjacent the proximal end of the plunger assists the physician in determining that the plunger is in the proper orientation for insertion into the handle.

The plunger is advanced distally, pushing the device into the incision along the then inward facing surface of the tunneler. The device thus follows the path defined by the tunneler to assure proper placement within the tissue. After insertion of the device, the handle and plunger are removed.

Various medical grade materials may be used to form the various parts of the subcutaneous implantation tool, for example, plastics, metals, rubber, sanitizable materials, etc. Exemplary embodiments of the subcutaneous implantation tool may be inexpensive, disposable, etc. The subcutaneous implantation tool may also be configured to be used with known automated injection systems, which use, e.g., compressed air or other inert gases in place of a manual plunger.

FIGS. 6A, 6B, 6C, 6D and 6E are distal end, cut-away, top, bottom and proximal end views, respectively, of the tool handle 100. In these views the projection 114 is visible. Projection 114 provides a distal facing stop surface limiting the insertion of the device 10 into the channel 102. It further engages the slot in the lower surface of the plunger 300, assuring proper orientation of the plunger within the handle. It also provides a proximal facing stop surface limiting distal movement of the plunger. The handle is also show as optionally provided with a slot 116 in its lower surface, through which advancement of the plunger and device can be observed.

Figure 7A:
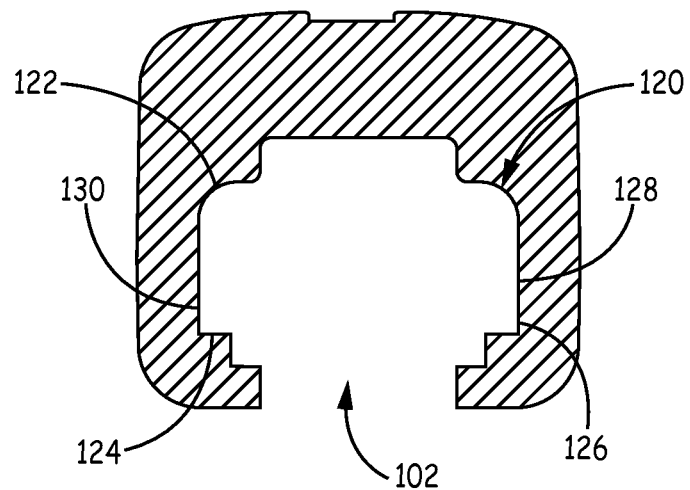
FIGS. 7A and 7B are cross sectional views through the tool handle as illustrated in FIG. 6C.
Figure 7B:
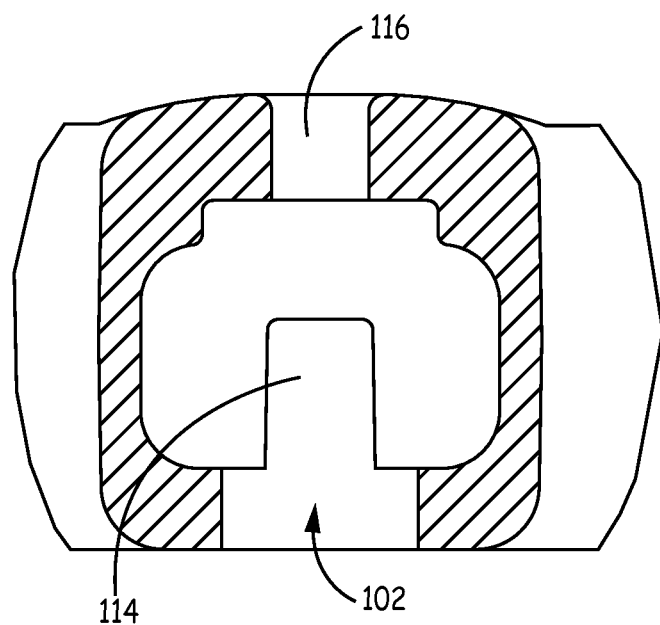

FIGS. 7A and 7B are cross sectional views through the tool handle as illustrated in FIG. 6C. In these views, the arrangement of the inner corner surfaces 12, 122, 124 and 126 can be seen. These surfaces, along with side surfaces 128 and 130, are arranged to generally correspond to the corners and the side surfaces of the device, preventing rotation of the device within the handle. The distal facing surface of projection 114 is also visible in this view.

FIGS. 8A, 8B, 8C and 8D are distal end, cut-away, top and proximal end views, respectively, of the plunger of 5B. In these figures, the configuration of the groove 306 can be seen, along with distally facing stop surface 310, which engages with the proximal facing surface of protrusion 114 of the handle, to limit distal movement of the plunger.

Figure 8B:
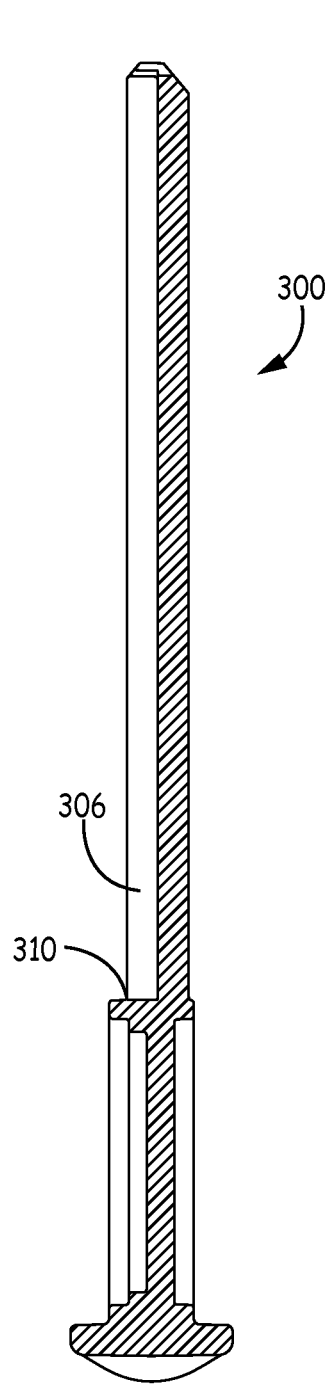
FIGS. 8A, 8B, 8C and 8D are distal end, cut-away, top and proximal end views, respectively, of the plunger of 5B.
Figure 8C:
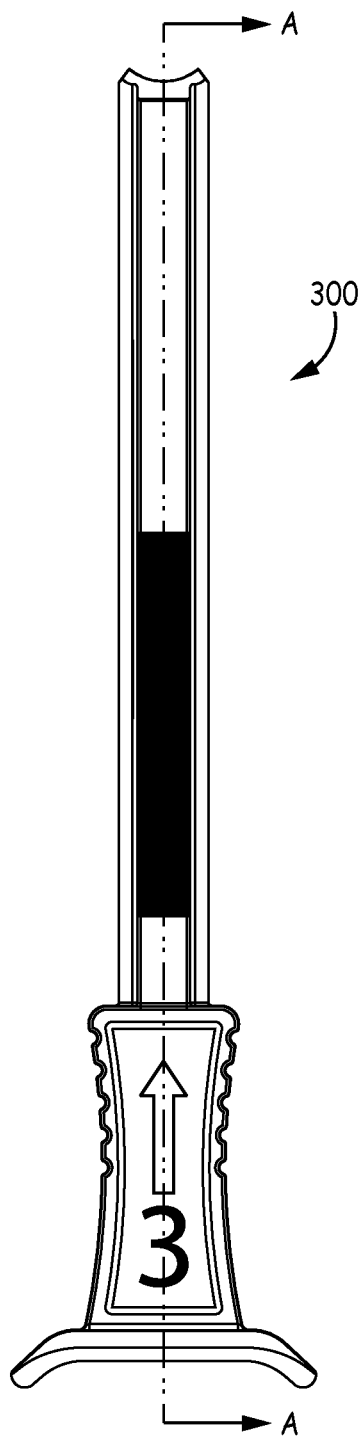
Figure 8A:
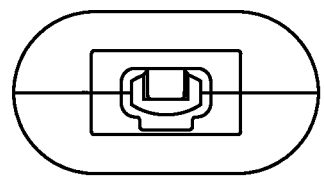
Figure 8D:
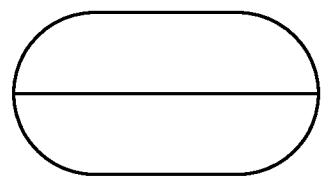

FIGS. 9A, 9B, and 9C are top, side and bottom views, respectively, of the plunger as illustrated in FIG. 8D. In these views, the configuration of the groove 306 is visible in more detail.

Figure 10:
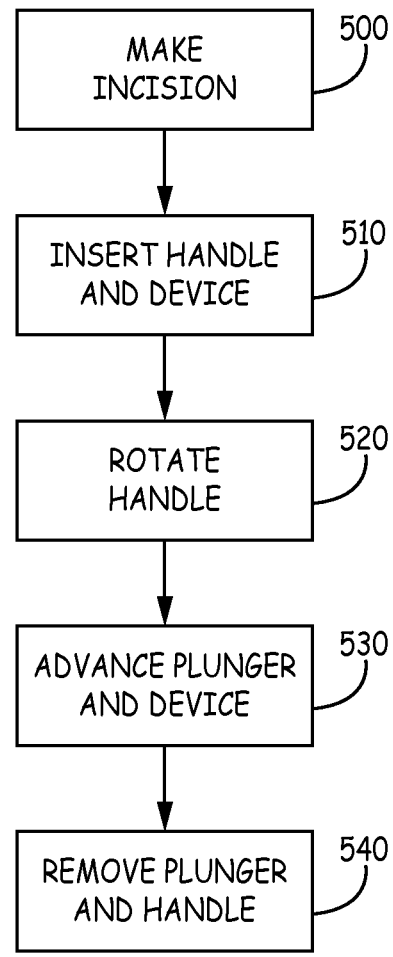

FIG. 10 is a flow chart illustrating a preferred embodiment of an insertion process according to the present invention. At 500, the incision is made using the incision tool. At 510, the handle carrying the device is inserted into the tissue such that the tunneler produces an elongated blunt incision along which the device may be advanced. In this step, the device is located outward of the tunneler relative to the patient's body. At 520 the handle, carrying the device is rotated so that the device is now inward of the tunneler relative to the patient's body. At 530, the device is advanced by the plunger along the handle and along the then inward facing surface of the tunneler subcutaneously into the patient's body. Finally, at 540, the handle and tunneler are removed.

Exemplary embodiments thus described allow for subcutaneous implantation of devices that are minimally invasive. Note that exemplary embodiments may be used in both human and animal patients.

Exemplary embodiments of the present invention being thus described, it will be obvious that the same may be varied in many ways. Such variations are not to be regarded as a departure from the spirit and scope of the exemplary embodiments of the invention, and all such modifications as would be obvious to one skilled in the art are intended to be included within the scope of the invention.

What is claimed is:

1. A system comprising:
   an implantable medical device comprising at least one electrode, the implantable medical device having an outer configuration defined by a width, a depth, and a length, the length of the implantable medical device being greater than each of the width and the depth of the implantable medical device; and
   an implantation tool configured to implant the implantable medical device in subcutaneous tissue, the implantation tool comprising:
      a one-piece handle, wherein the handle comprises:
         a channel section extending from a proximal end to a distal end along a longitudinal axis, the channel section defining a channel extending along the longitudinal axis, the channel terminating at a distal opening, wherein the channel is configured to receive the implantable medical device,
         wherein the channel defined by the channel section is defined to correspond to the outer configuration of the implantable medical device and engage one or more features of the outer configuration of the implantable medical device when the implantable medical device is received in the channel to prevent rotation of the implantable medical device within the channel, and
         wherein the channel is defined to correspond to a plurality of corners of the outer configuration of the implantable medical device and engage one or more of the plurality of corners when the implantable medical device is received in the channel; and
         an elongated tunneler fixedly extending longitudinally along the longitudinal axis from the distal end of the channel section, the tunneler being configured for blunt dissection of the subcutaneous tissue to produce a path through the subcutaneous tissue along which the implantable medical device is advanceable; and
         a plunger comprising a proximal end and a distal end, wherein the distal end of the plunger is configured to move in the channel defined by the channel section and push a proximal end of the implantable medical device to advance the implantable medical device distally from the channel section onto an exterior surface of the tunneler, and within the path produced by the tunneler.

2. The system of claim 1, wherein the elongated tunneler extends along a length from the distal end of the channel section, and wherein the length of the elongated tunneler is greater than the length of the implantable medical device.

3. The system of claim 1, wherein the channel defined by the channel section is configured to receive within the channel section the entire length of the implantable medical device.

4. The system of claim 1, wherein the elongated tunneler extends along the longitudinal axis from the distal end of the channel section to a tapered distal end of the tunneler.

5. The system of claim 1, wherein the channel is defined by at least a lower surface and one or more side surfaces, wherein the exterior surface of the elongated tunneler comprises an upper surface, wherein the distal end of the plunger is configured to move in the channel and push a proximal end of the implantable medical device to advance the implantable medical device when received in the channel along the lower surface of the channel through the distal opening and onto the upper surface of the tunneler.

6. The system of claim 1, wherein a greatest dimension of a cross-section of the tunneler orthogonal to the longitudinal axis is less than a greatest dimension of a cross-section of the channel orthogonal to the longitudinal axis.

7. The system of claim 1, wherein a greatest dimension of a cross section of the tunneler orthogonal to the longitudinal axis is substantially less than a greatest dimension of a cross section of the device body of the implantable medical device orthogonal to the length of the device body of the implantable medical device.

8. A system comprising:
   an implantable medical device comprising:
      at least one electrode; and
      a device body having an outer configuration defined by a width, a depth, and a length, the length of the device body being greater than each of the width and the depth of the device body; and
   an implantation tool configured to implant the implantable medical device in subcutaneous tissue, wherein the implantation tool comprises:
      a one-piece handle, wherein the handle comprises:
         a channel section extending from a proximal end to a distal end along a longitudinal axis, the channel section defining a channel extending along the longitudinal axis, the channel terminating at a distal opening, wherein the channel is configured to receive the implantable medical device, and
         an elongated tunneler fixedly extending longitudinally along the longitudinal axis from the distal end of the channel section, the tunneler configured for blunt dissection of the subcutaneous tissue to produce a path through the subcutaneous tissue along which the implantable medical device is advanceable; and
      a plunger comprising a proximal end and a distal end, wherein the distal end of the plunger is configured to move in the channel defined by the channel section and push a proximal end of the implantable medical device to advance the implantable medical device distally from the channel section onto an exterior surface of the tunneler, and within the path produced by the tunneler.

9. The system of claim 8, wherein the entire length of the device body of the implantable medical device is receivable within the channel defined by the channel section.

10. The system of claim 8, wherein the channel section defines the channel to correspond to the outer configuration of the device body to engage one or more features of the device body of the implantable medical device to prevent rotation of the implantable medical device within the channel.

11. The system of claim 8, wherein a length of the tunneler is greater than the length of the device body of the implantable medical device.

12. The system of claim 8, wherein a greatest dimension of a cross-section of the tunneler orthogonal to the longitudinal axis is substantially less than a greatest dimension of a cross-section of the device body of the implantable medical device orthogonal to the length of the device body of the implantable medical device.

13. The system of claim 8, wherein a distal end of the plunger is movable distally beyond the distal opening of the channel.

14. The system of claim 8,
wherein the tunneler extends longitudinally from the distal end of the channel section at a position laterally displaced from a location of the implantable medical device when the implantable medical device is received in the channel, and
wherein the exterior surface is a top surface of the tunneler extending from a bottom surface of the channel as a continuance of the bottom surface of the channel along the longitudinal axis.

15. The system of claim 8, further comprising an incision tool separate from the implantation tool, the incision tool configured to make an incision through which the implantation tool extends to deliver the implantable medical device.

16. The system of claim 15, wherein the incision tool comprises:
a flat, pointed blade, wherein a width of the blade defines a width of the incision; and
a curved handle connected to the blade, wherein the curved handle is designed to be held in a position allowing the blade to be advanced though skin and into the subcutaneous tissue at a shallow angle.

17. A system comprising:
an implantable medical device comprising at least one electrode; and
an implantation tool configured to implant the implantable medical device in subcutaneous tissue of a patient, the implantation tool comprising:
a handle, wherein the handle comprises:
a channel section extending from a proximal end to a distal end along a longitudinal axis, the channel section defining a channel extending along the longitudinal axis and terminating at a distal opening, wherein the channel is configured to receive the implantable medical device, and
an elongated tunneler protruding from the distal end of the channel section longitudinally along the longitudinal axis, the tunneler being configured for blunt dissection of the subcutaneous tissue to produce a path through the subcutaneous tissue along which the implantable medical device is advanceable,
wherein the tunneler extends longitudinally from the distal end of the channel section at a position laterally displaced from a location of the medical device when the medical device is received in the channel,
wherein a top surface of the tunneler extends from a bottom surface of the channel as a continuance of the bottom surface of the channel along the longitudinal axis, and
wherein the tunneler is configured to allow upward pressure on the handle to enlarge an incision into the subcutaneous tissue when a rotational position of the handle is such that the top surface of the tunneler faces inward relative to the patient and the implantable medical device is inward of the tunneler relative to the patient; and
a plunger comprising a proximal end and a distal end, wherein the distal end of the plunger is configured to move in the channel defined by the channel section and push a proximal end of the implantable medical device to advance the implantable medical device distally from the channel section alongside and exterior to the tunneler, and within the path produced by the tunneler, and wherein the distal end of the plunger is configured to move in the channel and push a proximal end of the implantable medical device to advance the implantable medical device when received in the channel along the lower surface of the channel through the distal opening and onto the top surface of the tunneler.

18. A system comprising:
an implantable medical device comprising at least one electrode, the implantable medical device having an outer configuration defined by a width, a depth, and a length, the length of the implantable medical device being greater than each of the width and the depth of the implantable medical device; and
an implantation tool configured to implant the implantable medical device in subcutaneous tissue, the implantation tool comprising:
a one-piece handle, wherein the handle comprises:
a channel section extending from a proximal end to a distal end along a longitudinal axis, the channel section defining a channel extending along the longitudinal axis, the channel terminating at a distal opening,
wherein the channel is configured to receive the implantable medical device, and
wherein the channel is defined by at least a lower surface, and further wherein at least an upper part of the channel section further defining the channel provides one or more openings configured to allow visual verification when the implantable medical device is being received in the channel; and
an elongated tunneler fixedly extending longitudinally along the longitudinal axis from the distal end of the channel section, the tunneler being configured for blunt dissection of the subcutaneous tissue to produce a path through the subcutaneous tissue along which the implantable medical device is advanceable; and
a plunger comprising a proximal end and a distal end, wherein the distal end of the plunger is configured to move in the channel defined by the channel section and push a proximal end of the implantable medical device to advance the implantable medical device distally from the channel section onto an exterior surface of the tunneler, and within the path produced by the tunneler.

19. A system comprising:
an implantable medical device comprising at least one electrode, the implantable medical device having an outer configuration defined by a width, a depth, and a length, the length of the implantable medical device being greater than each of the width and the depth of the implantable medical device; and
an implantation tool configured to implant the implantable medical device in subcutaneous tissue, the implantation tool comprising:
a one-piece handle, wherein the handle comprises:
a channel section extending from a proximal end to a distal end along a longitudinal axis, the channel section defining a channel extending along the longitudinal axis, the channel terminating at a distal opening,
wherein the channel is configured to receive the implantable medical device, and
wherein the channel is defined by at least a lower surface and further by at least an upper part of the channel section, wherein an opening is formed through at least a part of the lower surface to allow visual verification when the implantable medical device received in the channel is being advanced distally by the distal end of the plunger; and an elongated tunneler fixedly extending longitudinally along the longitudinal axis from the distal end of the channel section, the tunneler being configured for blunt dissection of the subcutaneous tissue to produce a path through the subcutaneous tissue along which the implantable medical device is advanceable; and a plunger comprising a proximal end and a distal end, wherein the distal end of the plunger is configured to move in the channel defined by the channel section and push a proximal end of the implantable medical device to advance the implantable medical device distally from the channel section to onto an exterior surface of the tunneler, and within the path produced by the tunneler.

20. A system comprising:

an implantable medical device comprising at least one electrode, the implantable medical device having an outer configuration defined by a width, a depth, and a length, the length of the implantable medical device being greater than each of the width and the depth of the implantable medical device; and an implantation tool configured to implant the implantable medical device in subcutaneous tissue, the implantation tool comprising:

a one-piece handle, wherein the handle comprises:

a channel section extending from a proximal end to a distal end along a longitudinal axis, the channel section defining a channel extending along the longitudinal axis, the channel terminating at a distal opening, wherein the channel is configured to receive the implantable medical device, and an elongated tunneler fixedly extending longitudinally along the longitudinal axis from the distal end of the channel section, the tunneler being configured for blunt dissection of the subcutaneous tissue to produce a path through the subcutaneous tissue along which the implantable medical device is advanceable; and a plunger comprising a proximal end and a distal end, wherein the distal end of the plunger is configured to move in the channel defined by the channel section and push a proximal end of the implantable medical device to advance the implantable medical device distally from the channel section onto an exterior surface of the tunneler, and within the path produced by the tunneler, wherein the channel section comprises:

a proximal opening at the proximal end of the channel section configured to allow insertion of the distal end of the plunger into the channel defined by the channel section, and a projection extending into the proximal opening corresponding to a mating groove defined by the plunger to only permit insertion of the distal end of the plunger into the proximal opening at the proximal end of the channel section in a certain orientation relative to the channel section.

21. The system of claim 20, wherein the projection extending into the proximal opening comprises a plunger stop surface for engagement with a stop surface of at an end of the groove defined by the plunger to limit distal movement of the distal end of the plunger.

22. The system of claim 20, wherein the projection extending into the proximal opening comprises a device stop surface for engagement with a surface of the implantable medical device when the implantable medical device is inserted into the channel to limit movement of the implantable medical device within the channel.

23. A system comprising:

an implantable medical device comprising at least one electrode, the implantable medical device having an outer configuration defined by a width, a depth, and a length, the length of the implantable medical device being greater than each of the width and the depth of the implantable medical device; and an implantation tool configured to implant the implantable medical device in subcutaneous tissue, the implantation tool comprising:

a one-piece handle, wherein the handle comprises:

a channel section extending from a proximal end to a distal end along a longitudinal axis, the channel section defining a channel extending along the longitudinal axis, the channel terminating at a distal opening, wherein the channel is configured to receive the implantable medical device, and an elongated tunneler fixedly extending longitudinally along the longitudinal axis from the distal end of the channel section, the tunneler being configured for blunt dissection of the subcutaneous tissue to produce a path through the subcutaneous tissue along which the implantable medical device is advanceable, wherein the tunneler extends longitudinally from the distal end of the channel section at a position laterally displaced from a location of the implantable medical device when the implantable medical device is received in the channel, and wherein a top surface of the tunneler extends from a bottom surface of the channel as a continuance of the bottom surface of the channel along the longitudinal axis; and a plunger comprising a proximal end and a distal end, wherein the distal end of the plunger is configured to move in the channel defined by the channel section and push a proximal end of the implantable medical device to advance the implantable medical device distally from the channel section onto the top surface of the tunneler, and within the path produced by the tunneler.

* * * * *